United States Patent [19]

Wallace

[11] Patent Number: 5,122,120
[45] Date of Patent: Jun. 16, 1992

[54] INTRAVASCULAR PLACEMENT APPARATUS

[75] Inventor: Henry G. Wallace, Colchester, United Kingdom

[73] Assignee: H G Wallace Ltd., Colchester, England

[21] Appl. No.: 574,474

[22] Filed: Aug. 28, 1990

[30] Foreign Application Priority Data

Aug. 31, 1989 [GB] United Kingdom ............... 8919728

[51] Int. Cl.$^5$ ............................................. A61M 5/00
[52] U.S. Cl. ................................. 604/164; 604/170
[58] Field of Search ............... 604/164, 165, 166, 167, 604/168, 169, 170

[56] References Cited

U.S. PATENT DOCUMENTS

| | | | |
|---|---|---|---|
| 4,046,144 | 9/1977 | McFarlane | 604/168 |
| 4,239,042 | 12/1980 | Asai | 604/164 |
| 4,349,023 | 9/1982 | Gross | 604/164 |
| 4,547,194 | 10/1985 | Moorehead | 604/905 |
| 4,596,557 | 6/1986 | Pexa | 604/86 |
| 4,629,450 | 12/1986 | Suzuki et al. | 604/167 |
| 4,705,511 | 11/1987 | Kocak | 604/167 |
| 4,721,506 | 1/1988 | Teves | 604/164 |
| 4,755,173 | 7/1988 | Konopka et al. | 604/167 |
| 4,772,267 | 9/1988 | Brown | 604/168 |
| 4,817,631 | 4/1989 | Schnepp-Pesch et al. | 604/167 |
| 4,824,433 | 4/1989 | Marz et al. | 604/164 |
| 4,832,696 | 5/1989 | Luther et al. | 604/164 |
| 4,842,591 | 6/1989 | Luther | 604/167 |
| 4,846,804 | 7/1989 | Davis et al. | 604/164 |
| 4,863,431 | 9/1989 | Vaillancourt | 604/170 |
| 4,935,010 | 6/1990 | Cox et al. | 604/122 |
| 4,952,207 | 8/1990 | Lemieux | 604/164 |
| 4,964,854 | 10/1990 | Luther | 604/168 |
| 4,966,588 | 10/1990 | Rayman et al. | 604/165 |
| 4,998,921 | 3/1991 | Vickroy et al. | 604/167 |
| 5,011,473 | 4/1991 | Gatturna | 604/164 |

FOREIGN PATENT DOCUMENTS

| | | |
|---|---|---|
| 0268480A1 | 5/1988 | European Pat. Off. . |
| 61-131746 | 6/1986 | Japan . |
| WO88/00842 | 2/1988 | PCT Int'l Appl. . |
| WO89/06553 | 7/1989 | PCT Int'l Appl. . |

OTHER PUBLICATIONS

EPO Search Report, EP 20 30 9264.
The Ultimate I.V. Catheter, 1977.
Cordis Lymphography Cannula Set, R. C. Stevens, 1966.

*Primary Examiner*—John J. Wilson
*Assistant Examiner*—Frank A. LaViola
*Attorney, Agent, or Firm*—Woodcock Washburn Kurtz Mackiewicz & Norris

[57] ABSTRACT

The invention provides an intravascular placement apparatus adapted for operative association with an introducer needle. The apparatus provides a cannula having a connector hub at its remote end, a self-sealing septum disposed across the internal lumen of the cannula whereby the cannula can be positioned by co-operation with the introducer needle, and a blunt hollow adaptor adapted to penetrate a channel in the septum. According to the invention, the self-sealing septum is formed from a resilient material which ages rapidly after forming to a point where its resilience is not significantly further affected by time. Preferably the channel is formed in situ in the septum when the septum has aged for a predetermined period.

13 Claims, 1 Drawing Sheet

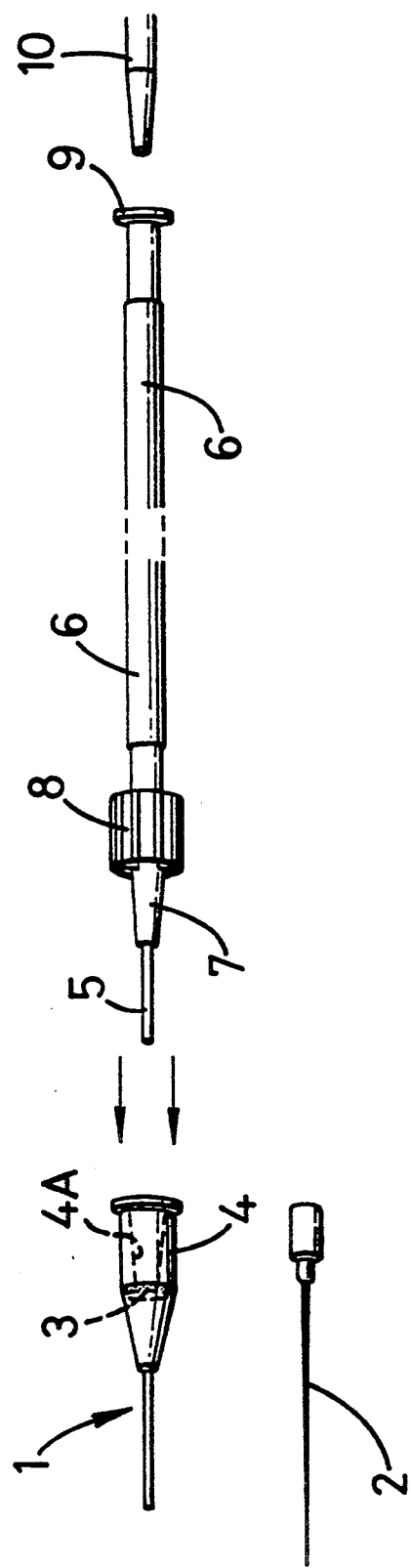

INTRAVASCULAR PLACEMENT APPARATUS

FIELD OF THE INVENTION

The present invention relates to an intravascular placement apparatus, and particularly to such an apparatus adapted to prevent the leakage of body fluids and to alleviate the problem of particles dislodged from a self-sealing septum blocking or interfering with the flow of a drug during administration.

BACKGROUND OF THE INVENTION

The intravascular placement of a plastics cannula by means of an introducer needle is a common medical procedure in order to administer fluids or drugs into the vascular system, or to sample or monitor blood therefrom. A typical method of utilising such an apparatus is to penetrate the skin and the subcutaneous tissue and thus enter, for example, a vein with a needle carrying a plastics cannula so that both can pass into the vein or the blood vessel. When the needle is withdrawn the plastics cannula is left in the vein and a hub disposed on the cannula at its remote end may then be coupled to an administration set or other suitable apparatus. However, during withdrawal of the needle from cannula blood escapes until the cannula is connected to said administration set or other apparatus.

Blood spillage during needle withdrawal can often be controlled by digital pressure on the skin adjacent the puncture to compress the vein ahead of the cannula tip. Peripheral veins have internal valves therein to prevent backflow of blood, and therefore pressure on the vein ahead of the cannula in the direction of flow of venus blood tends to control blood spillage from the cannula. This technique is effective but occupies both hands of the operator, is not possible with all veins, and requires a high level of competence. This problem has been addressed in our WO88/00842 which provides an intravascular placement apparatus adapted for operative association with an introducer needle; said apparatus comprising, a cannula provided with a connecter hub at its remote end, and a self-sealing septum disposed across the internal lumen of the cannula whereby the cannula can be positioned with the introducer needle. The use of a self-sealing septum prevents the back flow of blood or other fluids and allows the cannula to be positioned by less skilled staff.

The material from which the septum is formed is usually an elastomeric self-sealing rubber or plastics material. It has been known that a disadvantage of conventional needle tip designs, when utilised for co-operation with such an elastomeric septum is the problem of "coring". Coring occurs when the self-sealing septum material gets held in the needle lumen and either blocks the lumen or becomes discharged into the vascular system of the patient. This problem has been addressed in WO89/06553 (Baxter International Inc). The Baxter disclosure provides a blunt hollow adaptor at the distal end of an extension piece of a vascular placement apparatus so that the hollow adaptor will penetrate a pre-formed channel in the self-sealing septum and thereby form a channel from the extension piece to the cannula. The blunt hollow adaptor may be coupled directly to an administration set or via an extension piece, so that any change over in the administration set, for example to change one fluid for another, does not entail detachment of the adaptor from the cannula.

The rigid hollow adaptor is preferably formed of a metal or a rigid plastics material. An advantage of this last type of arrangement is that the substantially rigid blunt adaptor prevents needle-stick.

The arrangement of Baxter includes in a first aspect a thin pre-slit septum which may be penetrated by a blunt hollow adaptor. This arrangement is prone to problems in that after use over a number of engagement and disengagement cycles, the pre-slit disc shaped septum does not necessarily close entirely and this allows of the possibility of infection. In the second aspect of the Baxter disclosure there is provided a relatively large blunt hollow adaptor adapted to enter a pre-slit or partially pre-slit septum. The relatively large bore of the blunt adaptor necessarily causes an amount of collateral damage to the septum particularly when the resilient material of the septum has lost some of its resilience through aging.

SUMMARY OF THE INVENTION

We have now found that "coring" can be prevented, or at least reduced to a negligible problem, by providing an entire resilient septum, preferably associated with an introducer needle which both penetrates the septum, passes down the cannula and acts to assist the introduction of the cannula at the injection site.

Correctly used, the introducer needle will position the channel in the septum at a position, for example co-axial, where the blunt adaptor will be aligned with axis of the cannula. The pre-forming of the channel in the septum tends to result in mis-alignment of the channel with the blunt needle.

The performance of this arrangement is significantly improved if the resilient septum is of a bio-compatible plastic or rubber material with aging characteristics. As is well known some plastics materials and rubbers, for example natural rubbers, change their characteristics with age.

The invention therefore comprehends a resilient septum of a natural or synthetic resilient material which when initially positioned in its fresh state in the body of the vascular placement apparatus is fully resilient, thereby forming a good seal with the body components. After a given period of time, the resilient material ages such that relative hardness thereof is increased.

This allows the blunt hollow adaptor to penetrate the channel formed in septum by the introducer needle without displacing particles into the lumen of the same. The materials for the septum may be any synthetic or natural plastics or rubber materials which include an aging characteristic. The aging characteristic is the increase in hardness over a short aging period followed by a long period when the hardness does not significantly change as may be graphically characterised by a sigmate curve. An example of this material is bio compatible rubber but other synthetic plastic materials are available with these characteristics which are readily available to those skilled in the art by simple practical experimentation.

Accordingly the present invention is characterised in that the self-sealing septum is formed of a resilient material which ages rapidly after forming to a point where resilience is not significantly further affected by time, and in that a channel is formed in the septum when the septum has aged for the said pre-determined period of time.

BRIEF DESCRIPTION OF THE DRAWINGS

FIG. 1 is a view of the intravascular placement apparatus according to the current invention prior to assembly of the components.

DESCRIPTION OF THE PREFERRED EMBODIMENT

The present invention is characterized in that the self-sealing septum is formed of a resilient material which ages rapidly after forming to a point where resilience is not significantly further affected by time, and in that a channel is formed in the septum when the septum has aged for the said pre-determined period of time.

Preferably the resilient material is a biocompatible natural rubber and the pre-determined period of time is 2-5 weeks, most preferably about 3 weeks. It will be appreciated that the pre-determined period depends upon the precise constituents of the chosen material. We have found by use of this technique a that blunt hollow adaptor can be introduced into the septum without significant coring.

In a preferred form the invention the channel is formed by an introducer needle as hereinbefore described, in which case the hub assembly is most preferably provided with a convergent inner-profile to guide the introducer needle point to a position at which it is coaxial with the lumen of the cannula in use.

The hub may be adapted for connection with an extension piece carrying said blunt hollow adaptor; the operative end of the blunt hollow adaptor is preferably champhered to produce a low friction surface. The low friction surface may be achieved by electronic smoothing or by the provision of a low friction coating, for example "Teflon" (Registered Trade Mark).

One embodiment of the invention will now be described, by way of illustration only, with reference to the accompanying drawing which shows in plan, and in part cross-section, in arrangement in accordance to the present invention.

With reference to the drawing a plastics cannula (1) is formed with a hub assembly (4) which in this particular instance forms part of a Luer-lock of known type. The cannula (1) has a lumen such that it may be penetrated by an introducer needle (2) to an extent that the introducer needle (2) extends from the end of the cannula (1) in use.

The introducer needle (2) with the cannula (1) disposed thereabout may then be introduced into a blood vessel of a patient. The needle (2) may then be withdrawn leaving the cannula (1) in place.

In accordance with the present invention a self-sealing septum (3) formed of a bio-compatible natural rubber, is provided within the hub (4) on manufacture. This septum (3) is freshly manufactured before being positioned and is entire (i.e. has no channel therein).

An extension piece shown generally at (6) comprises a blunt hollow adaptor (5) which is interconnected with a Luer-taper (7). The Luer-taper (7) is provided with a Luer lock element (8) for inter-engagement with a Luer-lock arrangement on the periphery of the hub (4) in conventional fashion. The extension piece (6) is adapted to inter-connect the Luer-lock with a connector (9) remote therefrom for ready inter-connection of an administration set (10) or any other medical apparatus.

In use, the introducer needle (2) is urged through the septum (3) so that is passes along the cannula (1). It will be observed that interior faces of the hub (4) are tapered at (4A) to provide a relatively small "target area" and are still matched to the Luer-taper (7). The withdrawal of the needle (2) when the cannula (1) is located within the blood vessel then leaves the channel in the septum (3) which is sealed by the aged resilient material.

The blunt hollow adaptor (5) may then be introduced into the hub (4) and guided towards the central portion of the septum thereby. The blunt hollow adaptor contacts the septum (3) and an end portion thereof presses on the same and enters the channel. The end of adaptor (3) is thus guided into the channel formed by the introducer needle (2) to the extent that continued movement of the Luer-taper (7) towards the septum (3) causes the blunt hollow adaptor (5) to penetrate the septum (3) completely and thereby establish a self-sealed fluid path between the cannula (1) and adaptor (9). The Luer-lock element (8) may then be inter-engaged in the usual way with hub (4) thereby locking the two together.

An advantage of the intravascular placement apparatus in accordance to the present invention is that not only do neither the cannula (1) or the adaptor (5) require a sharp point and accordingly the danger of needle stick by this apparatus is largely speaking obviated, but also the problem of coring is at least substantially prevented.

I claim:

1. An intravascular placement apparatus adapted for operative association with an introducer needle, said apparatus comprising:

a) a cannula having a first operative end and a second end remote from said first end, said cannula provided with a connector hub at its remote end, b) a self-sealing septum having a surface portion and a portion interior thereto disposed across the internal lumen of the cannula, whereby the cannula can be positioned by co-operation with the introducer needle, and c) a blunt hollow adaptor adapted to penetrate a channel in the septum;

wherein the self-sealing septum is formed of resilient material, the surface portion of the septum being aged in a first aging step, thereby increasing its hardness, and wherein a channel having a surface in the interior portion of the septum is formed in the aged septum by inserting a needle through the septum after said first aging step, said needle being retained in the aged septum in a second aging step for a predetermined period during which the hardness of the channel surface increases, whereby after withdrawal of the needle following the second aging step the hardness of the surface portion is greater than the hardness of the channel surface and the hardness of the channel surface is greater than the hardness of the internal portion of the septum.

2. An apparatus according to claim 1, wherein the resilient material is a biocompatible natural rubber and the predetermined period of the second aging step is 2-5 weeks.

3. An apparatus according to claim 1, wherein the channel is formed by an introducer needle and wherein the connector hub is provided with a convergent profile to guide the introducer needle to a point which is generally coaxial with the lumen of the cannula.

4. An apparatus according to claim 1, wherein the hub is adapted for interconnection with an extension piece carrying said blunt hollow adapter and wherein the adapter has an operative end chamfered to produce a low friction surface.

5. A kit of parts which together form an intravascular placement apparatus comprising:
   a) a cannula having a first operative end and a second end remote from the first end, a connector hub formed on the second end;
   b) a self-sealing septum having a surface portion and a portion interior thereto disposed across the internal lumen of the cannula;
   c) a blunt hollow adapter adapted to penetrate a channel in the septum;
   d) an introducer needle sized to extend from the first operative end of the cannula when fully passed through the septum in which the needle is disposed; and wherein the self-sealing septum is formed of resilient material the surface portion of the septum being aged in a first aging step, thereby increasing its hardness, and wherein a channel having a surface in the interior portion of the septum is formed in the aged septum by an elongate element after said first aging step, said element being retained in the aged septum in a second aging step for a predetermined period during which the hardness of the surface of the channel increases, whereby after withdrawal of the needle following the second aging step the hardness of the surface portion is greater than the hardness of the channel surface and the hardness of the channel surface is greater than the hardness of the internal portion of the septum.

6. The apparatus according to claim 1, wherein the resilient material is a biocompatible natural rubber and the predetermined period of the second aging step is about 3 weeks.

7. An intravascular placement apparatus having (i) a needle and (ii) a cannula having a self-sealing septum formed from a resilient material, said septum having a surface portion and a portion interior thereto and disposed across the internal lumen of the cannula, said apparatus made by:
   a) forming said septum;
   b) initially aging said surface portion of said septum, thereby increasing its hardness;
   c) inserting said needle through said aged septum, thereby forming a channel having a surface in said interior portion of said septum;
   d) further aging said septum with said needle inserted therein for a predetermined period of time, thereby increasing the hardness of said channel surface, whereby the hardness of the surface portion is greater than the hardness of said channel surface and the hardness of the channel surface is greater than the hardness of said internal portion of said septum; and
   e) withdrawing said needle after said predetermined period of time.

8. The apparatus according to claim 7, wherein said septum is positioned within said cannula before said initial aging step.

9. The apparatus according to claim 7, wherein said resilient material is a biocompatible natural rubber and the predetermined period is in the range of 2-5 weeks.

10. The apparatus according to claim 7, further comprising a hollow adapter for connecting a medical device to said cannula, and wherein said apparatus is further made by inserting a portion of said hollow adapter through said channel after withdrawal of said needle.

11. The apparatus according to claim 7, wherein said septum has no channel formed therein until said needle is inserted therethrough.

12. In an intravascular placement apparatus having (i) a needle and (ii) a cannula having a self-sealing septum formed from a resilient material disposed across the internal lumen of the cannula, a method of preventing coring of said septum when a hollow adapter is inserted therethrough, comprising the steps of:
   a) forming said septum and then positioning said septum within said cannula;
   b) aging said septum, thereby increasing its hardness;
   c) inserting said needle through said aged septum, thereby forming a channel therein;
   d) further aging said septum with said needle inserted therein for a predetermined period of time, thereby further increasing the hardness of said septum;
   e) withdrawing said needle after said predetermined period of time; and
   f) inserting said hollow adapter through said channel in said septum.

13. The method according to claim 12, wherein said resilient material is a biocompatible natural rubber and the predetermined period is in the range of 2-5 weeks.

* * * * *